US012097053B2

(12) United States Patent
Wells et al.

(10) Patent No.: US 12,097,053 B2
(45) Date of Patent: Sep. 24, 2024

(54) METHOD OF OBTAINING X-RAY IMAGES

(71) Applicant: ADAPTIX LTD, Begbroke (GB)

(72) Inventors: Steve Wells, Marlow (GB); Gil Travish, Los Angeles, CA (US); Mark Evans, North Leigh (GB); Kristin Schmiedehausen, Los Altos, CA (US)

(73) Assignee: ADAPTIX LTD, Begbroke (GB)

( * ) Notice: Subject to any disclaimer, the term of this patent is extended or adjusted under 35 U.S.C. 154(b) by 381 days.

(21) Appl. No.: 17/573,880

(22) Filed: Jan. 12, 2022

(65) Prior Publication Data

US 2022/0133245 A1    May 5, 2022

Related U.S. Application Data

(63) Continuation of application No. PCT/GB2020/051483, filed on Jun. 19, 2020.

(30) Foreign Application Priority Data

Jul. 12, 2019  (GB) .................... 1910038

(51) Int. Cl.
*A61B 6/02*   (2006.01)
*A61B 5/08*   (2006.01)
(Continued)

(52) U.S. Cl.
CPC ............... *A61B 6/025* (2013.01); *A61B 5/08* (2013.01); *A61B 6/4007* (2013.01); *A61B 6/486* (2013.01)

(58) Field of Classification Search
CPC ......... A61B 6/025; A61B 5/08; A61B 6/4007; A61B 6/486; A61B 6/50; A61B 6/5205; A61B 6/541
See application file for complete search history.

(56) References Cited

U.S. PATENT DOCUMENTS 7,567,647 B1    7/2009 Maltz
10,893,838 B2 * 1/2021 Travish ............... A61B 6/4233
(Continued)

FOREIGN PATENT DOCUMENTS

EP    3064140    9/2016
JP    2012-000297    1/2012
(Continued)

OTHER PUBLICATIONS

UKIPO, Search Report in corresponding GB application GB1910038.7, Dec. 31, 2019.
(Continued)

*Primary Examiner* — Molly Wilburn
(74) *Attorney, Agent, or Firm* — Alley IP

(57) ABSTRACT

To obtain functional information 110 energising a first set of x-ray emitters of the panel over a first period of time and directing the x-rays at the first object; using the detector to detect the x-rays 35 after passing through the first object; processing the detected x-rays to create a first set of images to obtain tomosynthesis data 100; energising a second set of x-ray emitters of the panel over a second period of time and directing the x-rays at the first object; using the detector to detect the x-rays after passing through the first object; processing the detected x-rays to create a second set of images to obtain tomosynthesis data, wherein the number of emitters used in the second period of time is less than used in the first period of time; and comparing at least some images from each set of images to provide functional information.

14 Claims, 2 Drawing Sheets

(51) Int. Cl.
    *A61B 6/00*    (2024.01)
    *A61B 6/40*    (2024.01)

(56) References Cited

U.S. PATENT DOCUMENTS

| | | | |
|---|---|---|---|
| 2014/0010427 A1* | 1/2014 | Kriston | A61B 6/482 |
| | | | 382/131 |
| 2015/0139503 A1 | 5/2015 | Kabus et al. | |
| 2016/0106382 A1 | 4/2016 | Lu et al. | |
| 2016/0181053 A1 | 6/2016 | Wang et al. | |
| 2016/0256128 A1* | 9/2016 | Wang | A61B 6/025 |
| 2020/0118270 A1 | 4/2020 | Matsutani | |
| 2020/0286224 A1 | 9/2020 | Grass et al. | |
| 2021/0209818 A1 | 7/2021 | Travish et al. | |

FOREIGN PATENT DOCUMENTS

| | | |
|---|---|---|
| JP | 2013-230404 | 11/2013 |
| JP | 2015-521880 | 8/2015 |
| JP | 2018-148964 | 9/2018 |
| JP | 2019-506207 | 3/2019 |
| JP | 2020-534065 | 11/2020 |
| WO | 2017185028 | 10/2017 |

OTHER PUBLICATIONS

WIPO, International Search Report and Written Opinion in corresponding PCT application PCT/GB2020/051483, Sep. 30, 2020.
JPO, Notice of Reasons for Refusal in corresponding JP application 2022-502119, Mar. 26, 2024.

* cited by examiner

METHOD OF OBTAINING X-RAY IMAGES

RELATED APPLICATIONS

This application claims priority under 35 U.S.C. § 120 to, and is a continuation of, co-pending International Application PCT/GB2020/051483, filed Jun. 19, 2020 and designating the US, which claims priority to GB Application 1910038.7, filed Jul. 12, 2019, such GB Application also being claimed priority to under 35 U.S.C. § 119. These GB and International applications are incorporated by reference herein in their entireties.

FIELD

The present invention relates generally to a method of obtaining x-ray images and an x-ray imaging apparatus arranged to operate according to the method, and finds particular, although not exclusive, utility in generating 3D tomosynthesis images.

BACKGROUND

Diseases such as Chronic Obstructive Pulmonary Disease (COPD) are some of the leading global causes of morbidity and mortality. An understanding of the functioning of the lungs (as opposed to just their static anatomy) is essential for tackling such diseases and categorizing the severity of each case. Other examples affecting patients of diverse ages where regular assessments of lung function are required are asthma, lung cancer, pulmonary fibrosis and cystic fibrosis.

For the treatment of such diseases it is useful to have as much functional information relating to the relevant part of the body, as possible. Spirometry, which measures the volume of air being breathed in and out, gives an overall measure of lung function, but imaging methods are required to assess how different parts of the lungs are performing. However, the lungs, like certain other parts of the body move, making it difficult to produce clear images and/or obtain functional information about them.

Various different methods are known, however, they all have disadvantages as will be briefly described below.

The use of nuclear medicine involves the patient inhaling a radioactive gas which is then imaged by a gamma camera. This involves a relatively small radiation dose but the resultant images are 2D and low resolution with no anatomical reference. Furthermore, the procedure takes several minutes.

Standard chest x-rays with the patient holding their breath are quick to acquire and involve a relatively small radiation dose, but also only provide a 2D view with no functional information.

Dynamic x-ray imaging, in which repeated standard x-rays are acquired, is known and can provide functional images but involves a correspondingly higher dose and still only provides 2D images.

It is known that medical scanners can produce functional images through gated scans which involve monitoring the movement of an object, such as through the use of a monitoring belt worn by the patient, and taking repeated images when the object is in different positions. MRI scanners have the disadvantage of being expensive and time-consuming. Gated scans with CT scanners have the added disadvantage of involving a considerably higher radiation dose than repeated standard chest x-ray images These scanners also require the patient to lie down during the procedure which may be different from how the patient spends much of their daily life which may change the relative position of the various parts of the body.

Finally, it is known that tomosynthesis images can be produced by acquiring multiple x-ray projection images whilst moving an x-ray emitter, and possibly also moving the detector, during the procedure. In such cases the radiation dose is similar to that of a typical 2D x-ray image.

However, with current systems this is a relatively time-consuming process (taking around 5 to 12 seconds) so would not be suitable for obtaining multiple images during a breathing cycle to obtain functional information.

SUMMARY

It is therefore desirable to be able to produce relatively clear 3D tomosyntheses images of, and therefore obtain functional information about, a moving object, which is obscured by another object, with relatively low radiation dosage, and in as short a time as possible.

TABLE 1

Comparison of x-ray imaging systems

| Method | Approximate dose relative to a chest X-ray | Duration of scan |
|---|---|---|
| MRI | 0 | 30-60 mins |
| Chest X-ray | 1 times a chest x-ray | <1 s |
| Dynamic X-rays | 1.5 times a chest x-ray | a few seconds |
| Digital tomosynthesis | 1.8 times a chest x-ray | a few seconds |
| Nuclear medicine lung scan | 30-50 times a chest x-ray | 30 min |
| Static chest CT | 50 times a chest x-ray | a few minutes |
| Gated chest CT ("4DCT") | 200-400 times a chest x-ray | a few minutes |

The above table demonstrates how the use of digital tomosynthesis is able to create an interrogatable 3D image of an object, such as a human organ, with relatively low dosage and in a relatively short exposure time period.

In a first aspect, the present invention provides a method of obtaining x-ray images of a first object obscured by a second object, wherein the first object is moving relative to the second object; the method comprising the steps of:
  a) providing an x-ray imaging apparatus comprising a panel including an array of individually energisable x-ray emitters, a detector and a processor, wherein the array and the detector remain stationary relative to one another and at least a portion of the second object;
  b) energising a first set of x-ray emitters of the panel over a first period of time and directing the x-rays at the first object;
  c) using the detector to detect the x-rays after passing through the first object; d) processing the detected x-rays to create a first set of images to obtain tomosynthesis data showing the structure of the first object;
  e) energising a second set of x-ray emitters of the panel over a second period of time and directing the x-rays at the first object;
  f) using the detector to detect the x-rays after passing through the first object;
  g) processing the detected x-rays to create a second set of images to obtain tomosynthesis data showing the structure of the first object, wherein the number of emitters used in the second period of time is less than the number of emitters used in the first period of time; and
  h) comparing at least some images from each set of images to provide functional information relating to the density of the first object.

In this regard, the first object may be an organ, such as a lung or heart, or intestines, and the second object a body of a human or animal. The human or animal may be standing-up or lying down while the method is undertaken. The state of being stationary relates to the period during which x-rays are emitted and detected.

Since the number of emitters used in the second period of time is less than the number of emitters used in the first period of time, the dosage is reduced compared to simply repeating the energising of the first set of x-ray emitters. In this regard the subset area covered by the emitters used in the second period may be smaller than the area covered by the emitters used in the first time period. Alternatively, the second area may be approximately the same as the first area (or larger) but use a lower density (number per area) of emitters.

An advantage of the invention is that functional information may be derived about the first object, and an anatomical image of it may be obtained, in a single non-invasive method. This is an advantage over other methods which involve using separate devices to obtain anatomical and functional information. Furthermore, it avoids the need for translations to align anatomical and functional data from the different sources.

The tomosynthesis data may include, or form, an anatomical image/digital tomosynthesis image in which a set of planes through the first object are created. For visualization, the functional information may be superimposed onto the 3D anatomical information. For instance, the functional data may be displayed as an overlay on the anatomical planes.

Such methods may also allow an assessment of the ability to stretch (or resilience) of tissue (such as in a lung) during a breathing cycle. This may be useful for enabling the non-invasive diagnostic and characterization of disease progression for conditions such as emphysema (part of COPD) and pulmonary fibrosis, and may also allow characterization of lung cancer as it thought that cancerous cells locally change the elasticity of tissue.

The array of individually energisable x-ray emitters may be described as a distributed array of x-ray sources. These may emit x-rays through a range of angles and so pass through the first object at a range of angles enabling 3D digital tomosynthesis (DT) images to be derived. The use of a distributed array of x-ray sources allows each emitter to be individually electronically triggered which is much faster than having to physically move a single x-ray source. In addition, each emitter may only cover part of the field of view (first object). Therefore, it is possible to obtain repeat images from just a subset of the field of view. This means that the overall dose can be reduced compared to repeating the first set of emitters. The subset area may be defined by the second set of x-ray emitters of the panel which are energised over the second period of time.

The repeat images of each, or the, subset area may be used to obtain functional information. For example, changes in pixel intensity may be related to ventilation (an increased volume of air within the lung tissue may reduce its density and hence its x-ray attenuation).

Unlike CT, where x-rays are emitted over a complete 360-degree sweep around the patient, digital tomosynthesis only covers a partial sweep. In the present method of stationary tomosynthesis (sDT) the partial sweep is achieved without physical movement of the x-ray emitters by triggering a series of the spatially distributed fixed sources, in the array, fired in a sequence.

The array of x-ray emitters may be a single flat panel source (FPS). Alternatively, large areas such as a 40 cm by 40 cm x-ray detector for chest imaging may be provided by using an array of multiple flat panel sources operated in a coordinated manner, for example a 3 by 3 array of FPSs each with, for example, 25 electronically triggerable emitters. The FPS may be paired with a flat panel x-ray detector (FPD). The two devices may work in conjunction along with a computer that acts as an 'Acquisition Workstation' to process and analyse the detected x-rays as output from the FPD, and reconstruct multiple frames in to a 3D model which can be exported (often via a Picture Archiving and Communication System ('PACS')) to a 'Visualization Workstation' on which a Clinician may review the images using viewing software.

The detected x-rays used to derive the anatomical and functional images could be sequenced in a variety of ways. For example, an anatomical image may be acquired first as a typical DT image covering the full field of view. The patient may need to hold their breath for a few seconds. The patient would then be allowed to breath for a few breaths whilst functional images were acquired. During the breathing phase, a subset area or subset areas of the field of view would be imaged using the second set of x-ray emitters in the second period of time.

The target area of the second set of energised x-ray emitters may be determined by a clinician. However, other means are possible such as the use of pre-set locations relative to a fixed point, such as the centre of the field of view. Alternatively, the area(s)/location(s) may be automatically selected using pre-defined threshold values (for instance the lungs typically have considerably lower x-ray attenuation than the surrounding tissue).

The images may comprise pixels, each pixel having a value assigned to it on the basis of its intensity, with the value lying on a scale. The functional information relating to the density of the first object may be provided by a step of analysing changes in the pixel intensity in the comparison between each set of images.

For instance, the step of analysing changes in the pixel intensity in the comparison may include determining the standard deviation change in the values between the first and second sets of images.

The images may be in greyscale format, or may be in colorimetric (or more specifically photometric) grayscale format. The images may lie in a colourspace.

The functional information relating to the density may relate to relative density between various imaged portions included in the imaged object. The functional information relating to the density may relate to changes in density of at least a portion of the imaged object.

The first and second time periods may overlap at least partially. In other words, the start time of one set may occur before the end time of another set. Some of the detected x-rays from the first period of time may be excluded from the first set of images in the processing step d). Some of the detected x-rays from the second period of time may be excluded from the second set of images in the processing step g).

The first and second time periods may each have a start and end point, and the method may include the steps of: providing a movement detector to monitor the movement of the first object; and determining the start and end points of each of the first and/or second time periods as a result of the movement of the first object. A respiratory band may be used as the movement detector to record the breathing phases so that these may be correlated by the processing means to the created images.

Other means for monitoring the movement of the first object are contemplated such as monitoring the position of anatomical landmarks. For instance, during a breathing cycle.

The method may include the step of temporarily reducing or eliminating the movement of the first object. This may be achieved by applying mechanical force to the first or second object. For instance, the most common approach to reducing patient motion is physical restraint, including straps, bars, cushions and other accessories used to prevent the gross motion of a patient's body part. Alternatively, or additionally, breath-holding is a common method for reducing patient motion, assuming they are well enough to maintain the hold. Breath holds have the advantage of reducing internal motion, and specifically of changes in the lung volume and movement of the surrounding tissues and organs. Controlling the breathing rate can also be achieved through a mechanical ventilator. Often patients whose lung function is compromised are already on ventilation and therefore the ventilator diagnostic may be used to control the timing of x-ray application. In cases where the breathing pace (or amount of lung inflation) is important to know, but not control, a simple sensor may be applied to the chest wall and used to control the x-ray timing or tag the x-ray images.

Chemical "restraints" may also be used, especially in veterinary or paediatric cases. For patients that are unable to sit still or be easily restrained, methods such as mild sedation or general anaesthesia may be employed.

At least some of the first set of images may also be used in the creation of the second set of images.

The method may further comprise the steps of subsequently energising the second set of x-ray emitters of the panel over subsequent repeated periods of time and directing the x-rays at the first object; using the detector to detect the x-rays after passing through the first object; processing at least some of the subsequently detected x-rays to create subsequent repeated sets of images of the first object.

In this connection, the subset area may be exposed to x-rays from one or more emitter, wherein the conelets produced by each emitter may overlap one another at the detector. The degree of overlap may be relatively minimal. The one or more emitters may be repeatedly energised. This may allow 2D images and measurements to be derived such as the change in pixel intensity as a measure of ventilation.

Alternatively, a set of emitters with greater relative overlap may be repeatedly energised covering the subset area. This may allow 3D digital tomosynthesis images and information to be derived. For example, monitoring motion as a measure of elasticity.

If more than one subset area is required to be imaged then one or more of these areas may be exposed to the x-rays simultaneously, or at least with some temporal overlap. This may be the case where there is minimal spatial overlap of the subset areas.

The method may further comprise the step of comparing at least some images from each set of images from the second and subsequent sets of images to provide functional information about the first object.

The functional information provided about the first object may relate to one or more of its composition, its size, its shape, its location relative to the second object, its elasticity, and its density. It may also relate to one or more of its movement pattern, movement rate and movement positions. Functional information may include identifying its boundary, for example, a lung boundary area, or calculating the x-ray attenuation of different regions of the first object and calculating how this changes over time, such as in a breathing cycle. This could be done in 3D, or by measuring the projected 2D boundary changes (as a proxy indicator for volume), or by measuring changes in attenuation in 2D projections.

Furthermore, the movement of image 'texture' may be tracked to assess motion of the whole or parts of the first object. It is to be understood that the method may include the step of varying the angle of each conelet of x-rays. In this regard, in typical use, an x-ray beam may be conical in shape, thus forming a conelet. A "conelet" may refer to the generally conical envelope of the x-ray emission from a single emitter. The term may be used to distinguish the emission of a single emitter from that of the overall array of emitters.

For a typical anatomical tomosynthesis image of the lungs conelets between 20° and 40° wide may be appropriate. In this regard, the angle may be the angle of the cone measured at its apex, or may be half that angle (in other words, the angle between the normal from the emitter and a side of the cone). However, for repeated 2D functional imaging of subset areas of an object narrower cones may be preferred.

Generally circular or elliptical x-ray projections may be used, although other shapes such as semi-circles or more rectangular geometries are contemplated. Masks or other means may be used to define the shapes.

During processing of the images, movement of the first object may be taken account of by the use of processing (such as by the use of software) to control or correct for motion. For instance, the method may include the steps of placing markers on a patient's body, and using cameras to track gross motion. These video (optical) based motion tracking tools may be useful for correcting certain kinds of motion and may even track the breathing rate. Other steps may include the use of structured light projected onto a patient's body and imaged to obtain 3D (depth) information and hence track motion on a smaller spatial scale. X-ray markers may also be used to indicate specific areas and may be used to track relative motion within the x-ray images. For instance, a marker placed next to a shoulder may be compared to one placed on the chest to look for relative movement.

Collectively these methods may be used to pre- or post-process the x-ray image data. For instance, if breathing motion is to be analysed in the x-ray, it may be possible to eliminate gross motion by taking the optical (video) motion data and pre-processing the x-ray data to remove overall body sway while preserving the movement due to breathing. Similarly, the data could be pre-processed by removing the motion of the shoulder placed marker(s) if using the x-ray based motion detection. Conversely, it may be desirable to post-process the data by, for instance, tracking the lung motion optically, and selecting or sorting the x-ray frames according to this breath-cycle data.

In a second aspect, the invention provides an x-ray imaging apparatus arranged to operate according to the first aspect. The movement detector may be a respiratory band. The mechanical force may be applied by a forced air ventilator.

BRIEF DESCRIPTION OF THE DRAWINGS

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

FIG. 1 is a schematic view of x-ray apparatus in use.

DETAILED DESCRIPTION

Figure 1:
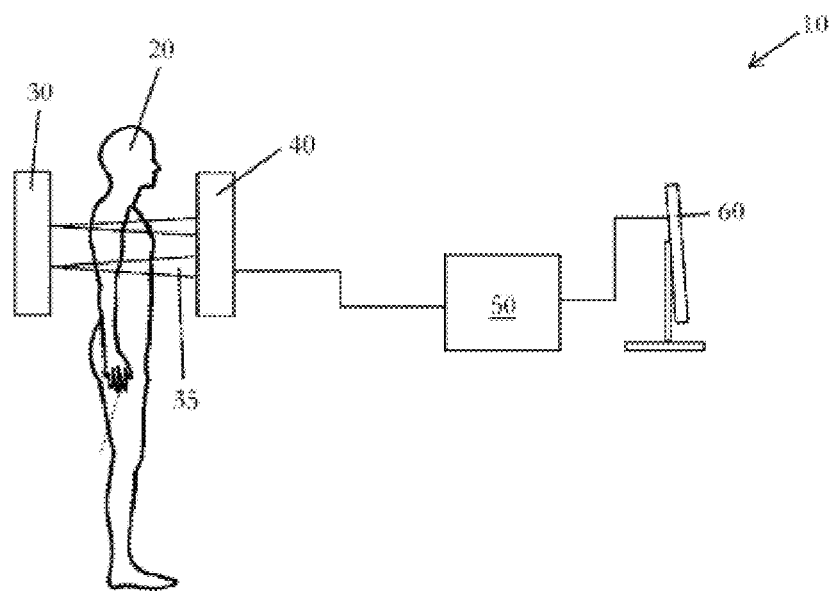

The present invention will be described with respect to certain drawings but the invention is not limited thereto but only by the claims. The drawings described are only schematic and are non-limiting. Each drawing may not include all of the features of the invention and therefore should not necessarily be considered to be an embodiment of the invention. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that operation is capable in other sequences than described or illustrated herein. Likewise, method steps described or claimed in a particular sequence may be understood to operate in a different sequence.

Moreover, the terms top, bottom, over, under and the like in the description and the claims are used for descriptive purposes and not necessarily for describing relative positions. It is to be understood that the terms so used are interchangeable under appropriate circumstances and that operation is capable in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Similarly, it is to be noticed that the term "connected", used in the description, should not be interpreted as being restricted to direct connections only. Thus, the scope of the expression "a device A connected to a device B" should not be limited to devices or systems wherein an output of device A is directly connected to an input of device B. It means that there exists a path between an output of A and an input of B which may be a path including other devices or means. "Connected" may mean that two or more elements are either in direct physical or electrical contact, or that two or more elements are not in direct contact with each other but yet still co-operate or interact with each other. For instance, wireless connectivity is contemplated.

Reference throughout this specification to "an embodiment" or "an aspect" means that a particular feature, structure or characteristic described in connection with the embodiment or aspect is included in at least one embodiment or aspect of the present invention. Thus, appearances of the phrases "in one embodiment", "in an embodiment", or "in an aspect" in various places throughout this specification are not necessarily all referring to the same embodiment or aspect, but may refer to different embodiments or aspects. Furthermore, the particular features, structures or characteristics of any one embodiment or aspect of the invention may be combined in any suitable manner with any other particular feature, structure or characteristic of another embodiment or aspect of the invention, as would be apparent to one of ordinary skill in the art from this disclosure, in one or more embodiments or aspects.

Similarly, it should be appreciated that in the description various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Moreover, the description of any individual drawing or aspect should not necessarily be considered to be an embodiment of the invention. Rather, as the following claims reflect, inventive aspects lie in fewer than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some features included in other embodiments, combinations of features of different embodiments are meant to be within the scope of the invention, and form yet further embodiments, as will be understood by those skilled in the art. For example, in the following claims, any of the claimed embodiments can be used in any combination.

In the description provided herein, numerous specific details are set forth. However, it is understood that embodiments of the invention may be practised without these specific details. In other instances, well-known methods, structures and techniques have not been shown in detail in order not to obscure an understanding of this description.

In the discussion of the invention, unless stated to the contrary, the disclosure of alternative values for the upper or lower limit of the permitted range of a parameter, coupled with an indication that one of said values is more highly preferred than the other, is to be construed as an implied statement that each intermediate value of said parameter, lying between the more preferred and the less preferred of said alternatives, is itself preferred to said less preferred value and also to each value lying between said less preferred value and said intermediate value.

The use of the term "at least one" may mean only one in certain circumstances. The use of the term "any" may mean "all" and/or "each" in certain circumstances.

The principles of the invention will now be described by a detailed description of at least one drawing relating to exemplary features. It is clear that other arrangements can be configured according to the knowledge of persons skilled in the art without departing from the underlying concept or technical teaching, the invention being limited only by the terms of the appended claims.

In FIG. 1 an x-ray apparatus 10 is shown including a flat panel emitter array 30, emitting x-rays through the chest of a patient 20. The x-rays are detected by a detector panel 40 opposite the emitter array 30.

The resultant data is sent to a processor 50 where it may be processed to create images viewable on a screen 60.

Only two cones of x-rays 35 are shown, however, it is to be understood that in use, more x-ray cones may be emitted simultaneously and/or consecutively as required during the process.

Figure 2:
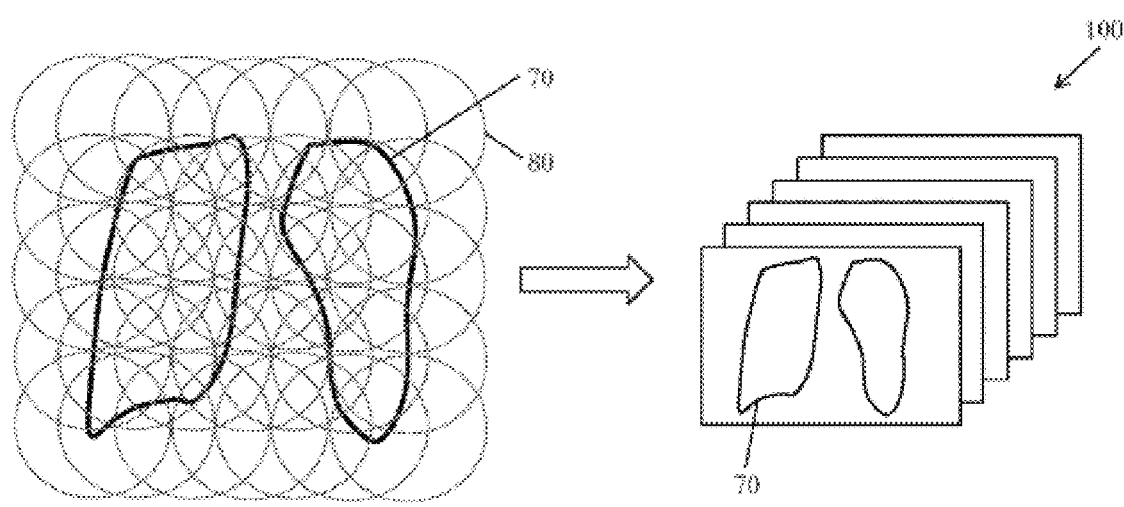
FIG. 2 is a schematic view of a pair of lungs being x-rayed to create a 3D anatomical digital tomosynthesis dataset.

FIG. 2 shows a pair of lungs 70 covered by an overlapping series of circles 80. Each circle 80 is indicative of the area covered by an emitter's conelet of x-rays. In reality, the size of the circles may be larger or smaller, and the number of circles may be greater or less, than shown. It is contemplated that shapes other than circles may be employed.

This series may be produced after the following steps have been undertaken: energising a first set of x-ray emitters of the panel over a first period of time and directing the x-rays at the first object and using the detector to detect the x-rays after passing through the first object.

Using known processing techniques, it is possible to use the information gathered by the detector to create a 3D tomosynthesis model of the lungs. This information may be presented in the form of slices 100 such that a clinician may view the lungs at various depths through their thickness.

Figure 3:
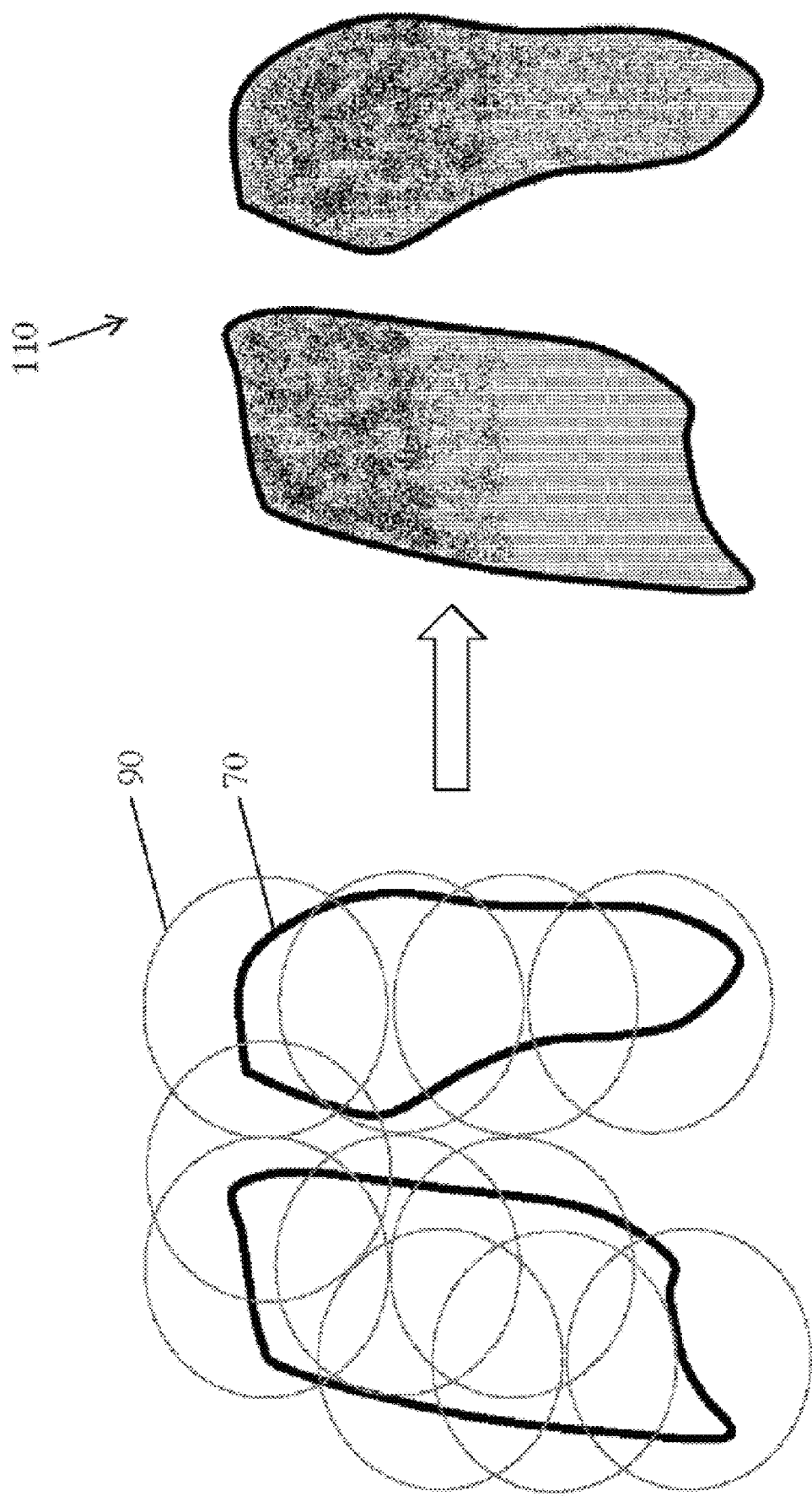
FIG. 3 is a schematic view of a pair of lungs being x-rayed in a different manner to that of FIG. 2 to derive functional data about the lungs.

In FIG. 3 the same pair of lungs 70 is shown. However, only a few circles 90 are shown. This is an example of a smaller subset area which is exposed to a second set, and possibly subsequent sets, of x-rays, possibly several times during movement of the lungs. This may be effected by energising only selected emitters. In this example, as well as covering a smaller subset area, the density of conelets covering the area is reduced relative to the area covered by the first set of x-rays. Once the x-rays are detected by the detector and processed by the processor a second and possibly subsequent set of images of the lungs may be created. These sets of images may be compared to one another, and to the first set, to determine functional information about the lungs. Such functional information may be presented graphically, for instance as a colour overlay on an image of the lungs. The overlay may depict functional information such as, for instance, the magnitude of difference between lung inflation and deflation 110. Functional measures may be shown as a number, or a colour, as an overlay onto the aligned stack of DT slices.

The density of the object may be determined from the shade of the image; darker shades indicating areas of denser material than lighter shades. The density of the object may change during time (for instance as a lung is inflated and deflated). The density may change at different rates in different portions of the object. The density (of the object, or at least one portion of the object) determined in each set of images may be compared to that in another set of images, and determined changes in the density may be indicated graphically. The comparison may be undertaken by a processor. The step of analysing changes may be made by a comparison of pixel intensity, where each pixel has a value assigned to it on the basis of its intensity, with the value lying on a scale. For instance, the step of analysing changes in pixel intensity in the comparison may include determining standard deviation change in the values between the first and second sets of images.

The second and subsequent x-ray imaging may use specific locational landmarks in the lungs to aid the determination of physical changes during a breathing cycle.

It is to be understood that some of the first set of images, obtained during the first x-ray emission period, may be used when processing the second and subsequent sets of images. The sets may be interleaved. In this way, the radiation dosage received by the patient may be reduced.

The comparison of images from the various sets of images may be undertaken on the basis that certain images are created of the same location, possibly using the same emitters. Alternatively, or additionally, the comparison may be undertaken on the basis that certain images are created at the same point during the movement (e.g. breathing) cycle. This may be determined by the use of a monitor such as a breathing sensor.

Although this method and apparatus have been described with respect to patients and the derivation of medical information, it is to be understood that they could be used with respect to other matters where a first moving object is obscured by a second stationary object. For instance, the analysis of luggage.

The invention claimed is:

1. A method of obtaining x-ray images of a first object obscured by a second object, wherein the first object is moving relative to the second object; the method comprising the steps of:
   a) providing an x-ray imaging apparatus comprising a panel including an array of individually energisable x-ray emitters, a detector and a processor, wherein the array and the detector remain stationary relative to one another and at least a portion of the second object;
   b) energising a first set of x-ray emitters of the panel over a first period of time and directing the x-rays at the first object;
   c) using the detector to detect the x-rays after passing through the first object;
   d) processing the detected x-rays to create a first set of images to obtain tomosynthesis data showing the structure of the first object;
   e) energising a second set of x-ray emitters of the panel over a second period of time and directing the x-rays at the first object;
   f) using the detector to detect the x-rays after passing through the first object;
   g) processing the detected x-rays to create a second set of images to obtain tomosynthesis data showing the structure of the first object, wherein the number of emitters used in the second period of time is less than the number of emitters used in the first period of time; and
   h) comparing at least some images from each set of images to provide functional information relating to changes in density of at least one portion of the first object.

2. The method of claim 1, wherein the images comprise pixels, each pixel having a value assigned to it on the basis of its intensity, with the value lying on a scale, and wherein the functional information relating to the density of the first object is provided by a step of analysing changes in the pixel intensity in the comparison between each set of images.

3. The method of claim 2, wherein the step of analysing changes in the pixel intensity in the comparison includes determining the standard deviation change in the values between the first and second sets of images.

4. The method of claim 1, wherein the first and second time periods overlap at least partially.

5. The method of claim 1, wherein some of the detected x-rays from the first period of time are excluded from the first set of images in the processing step d).

6. The method of claim 1, wherein some of the detected x-rays from the second period of time are excluded from the second set of images in the processing step g).

7. The method of claim 1, wherein the first and second time periods each have a start and end point, and the method includes the steps of: providing a movement detector to monitor movement of the first object; and determining the start and end points of each of the first and/or second time periods as a result of the movement of the first object.

8. The method of claim 1, including the step of temporarily reducing or eliminating movement of the first object.

9. The method of claim 8, wherein the step of temporarily reducing or eliminating the movement of the first object is achieved by applying mechanical force to the first or second object.

10. The method of claim 1, wherein at least some of the first set of images are also used in the creation of the second set of images.

11. The method of claim 1, further comprising the steps of subsequently energising the second set of x-ray emitters of the panel over subsequent repeated periods of time and directing the x-rays at the first object; using the detector to detect the x-rays after passing through the first object; processing at least some of the subsequently detected x-rays to create subsequent repeated sets of images of the first object.

12. An x-ray imaging apparatus arranged to operate according to the method of claim 1.

13. An x-ray imaging apparatus arranged to operate according to the method of claim 7, wherein the movement detector is a respiratory band.

14. An x-ray imaging apparatus arranged to operate according to the method of claim 9, wherein the mechanical force is applied by a forced air ventilator.

* * * * *